United States Patent
Ouazzani et al.

(10) Patent No.: US 9,751,826 B2
(45) Date of Patent: Sep. 5, 2017

(54) 4-VINYL-2-CYCLOPENTEN-1-ONE DERIVATIVES, THE PRODUCTION THEREOF, AND THE USE OF SAME AS AN ANTIBIOTIC AGENT

(71) Applicant: Centre National de la Recherche Scientifique (CNRS), Paris (FR)

(72) Inventors: Jamal Ouazzani, Massy (FR); Emilie Adelin, Massy (FR); Geraldine Le Goff, Antony (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 15/308,936

(22) PCT Filed: May 6, 2015

(86) PCT No.: PCT/EP2015/059999
§ 371 (c)(1),
(2) Date: Nov. 4, 2016

(87) PCT Pub. No.: WO2015/169876
PCT Pub. Date: Nov. 12, 2015

(65) Prior Publication Data
US 2017/0121269 A1 May 4, 2017

(30) Foreign Application Priority Data

May 6, 2014 (FR) ..................... 14 54090

(51) Int. Cl.
*C07C 69/738* (2006.01)
*C07C 45/59* (2006.01)
*C07C 67/475* (2006.01)
*C12P 7/26* (2006.01)
*C12P 7/62* (2006.01)

(52) U.S. Cl.
CPC ............ *C07C 69/738* (2013.01); *C07C 45/59* (2013.01); *C07C 67/475* (2013.01); *C12P 7/26* (2013.01); *C12P 7/62* (2013.01); *C07C 2101/10* (2013.01)

(58) Field of Classification Search
CPC ..... C07C 69/738; C07C 45/59; C07C 67/475; C07C 2101/10; C12P 7/26; C12P 7/62
See application file for complete search history.

(56) References Cited

FOREIGN PATENT DOCUMENTS

JP 60-152443 8/1985

OTHER PUBLICATIONS

Elkhateeb et al., *New Terpenes from the Egyptian Soft Coral Sarcophyton ehrenberti*, Mar. 12 Drugs 1977-1986 (2014).
Gavina et al., *Existence and Reactivity of Bicyclic Annulenones. 4-Phenylbicyclo[3.3.0]octa-1(5),3,6-triene-2,8-dione*, 49 J. Org. Chem. 4616-4618 (1984).
Ulbrich et al., *Microwave- or Microreactor-Assisted Conversion of Furfuryl Alcohols into 4-Hydroxy-2-cyclopentenones*, 13 Cluster 2037-2040 (2010).
International Search Report mailed on Aug. 27, 2015, in corresponding PCT Application No. PCT/EP2015/059999.
International Preliminary Report mailed on Jan. 13, 2015, in corresponding French Application No. FR 1454090.

*Primary Examiner* — Sudhakar Katakam
(74) *Attorney, Agent, or Firm* — Buchanan Ingersoll & Rooney PC

(57) ABSTRACT

The invention relates to a compound of general formula (I) wherein: R1 is a hydrogen atom or a C1 to C4 alkyl radical; R2 is a C1 to C4 hydroxyl or alkoxyl radical; and R3 and R4 are independently a hydrogen atom or a C1 à C4 alkyl radical; and the enantiomers and mixtures of enantiomers thereof, especially in a racemic form.

7 Claims, 7 Drawing Sheets

Figure 1:
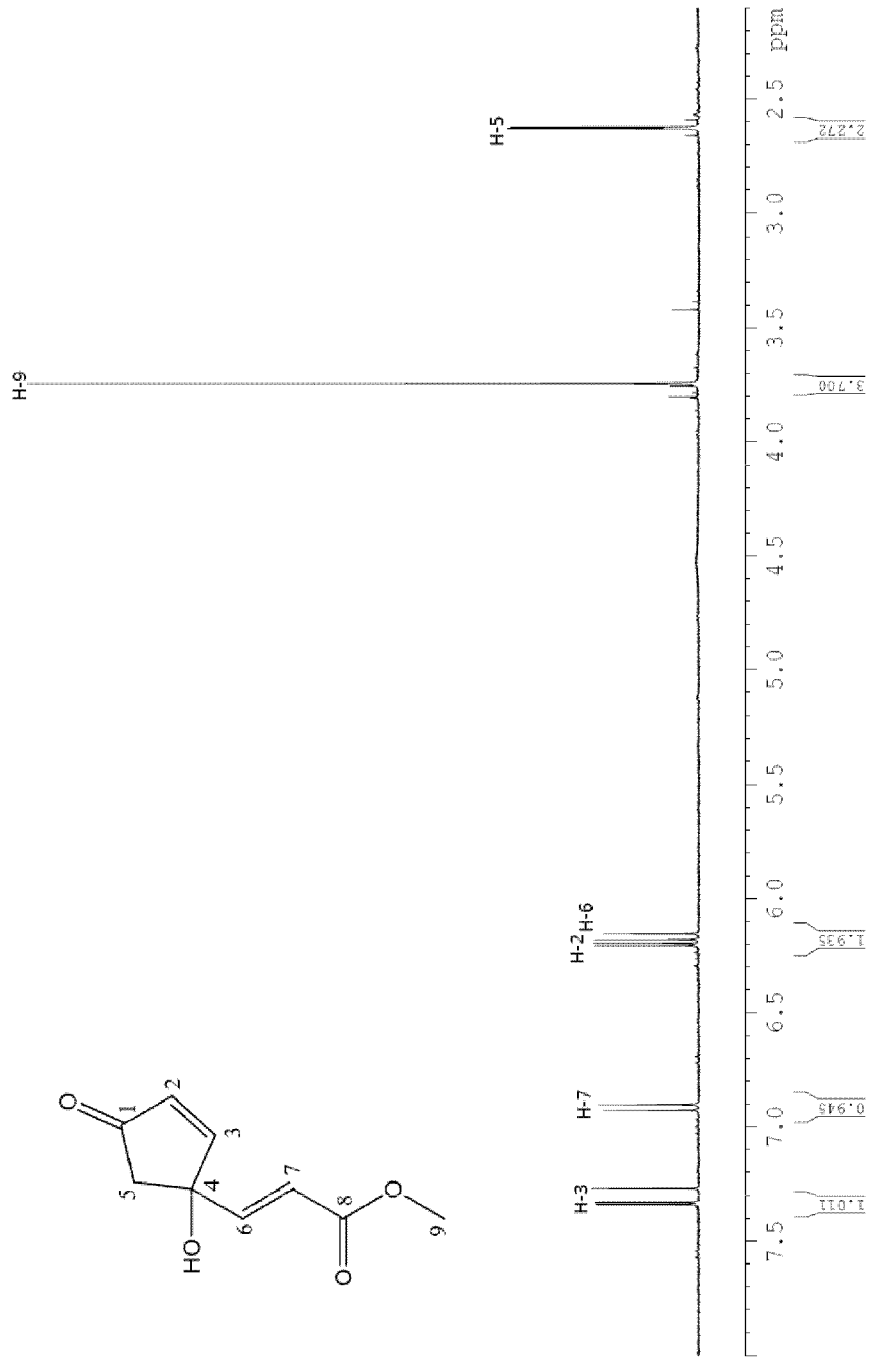
Figure 2:
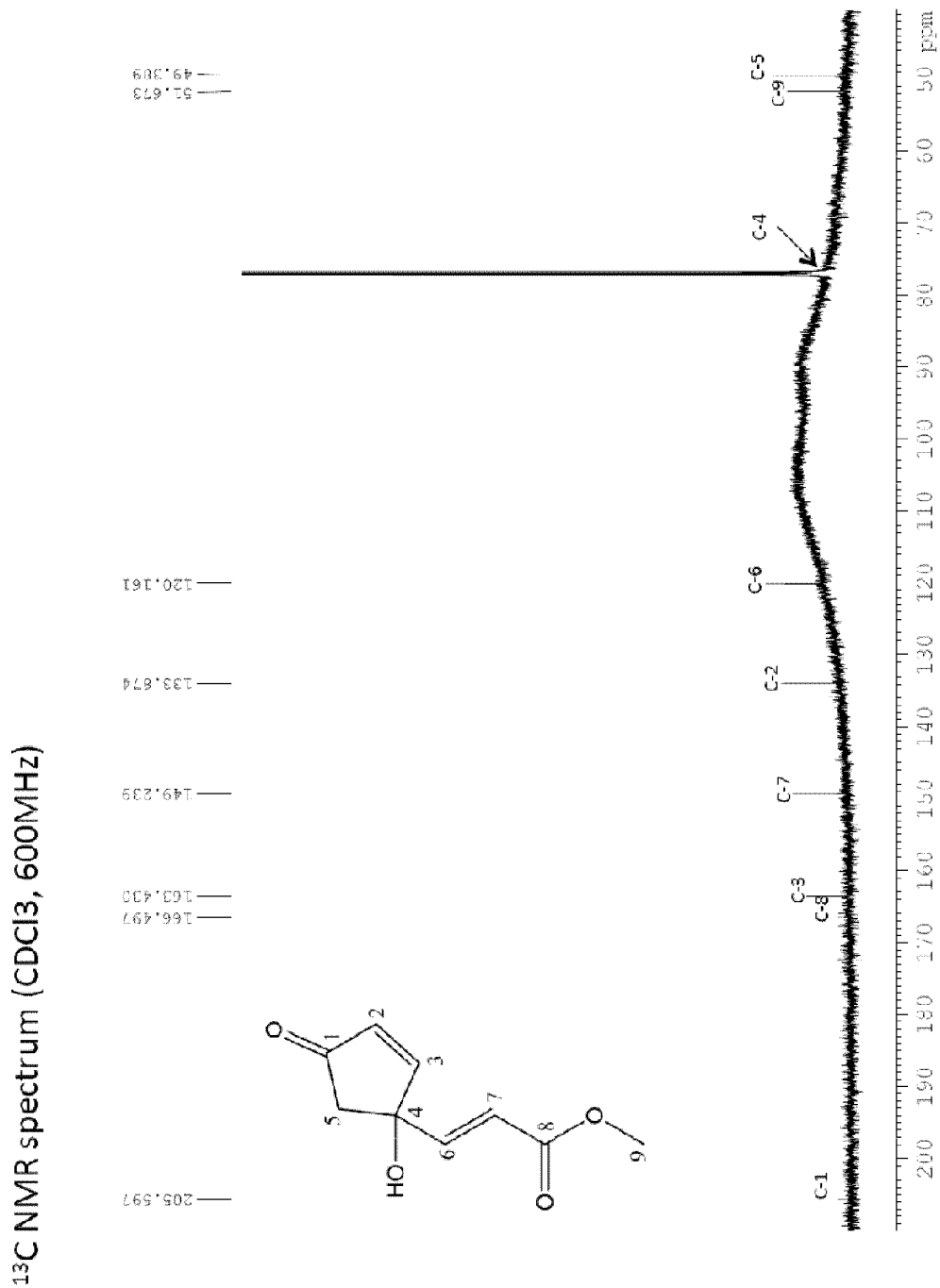
Figure 3:
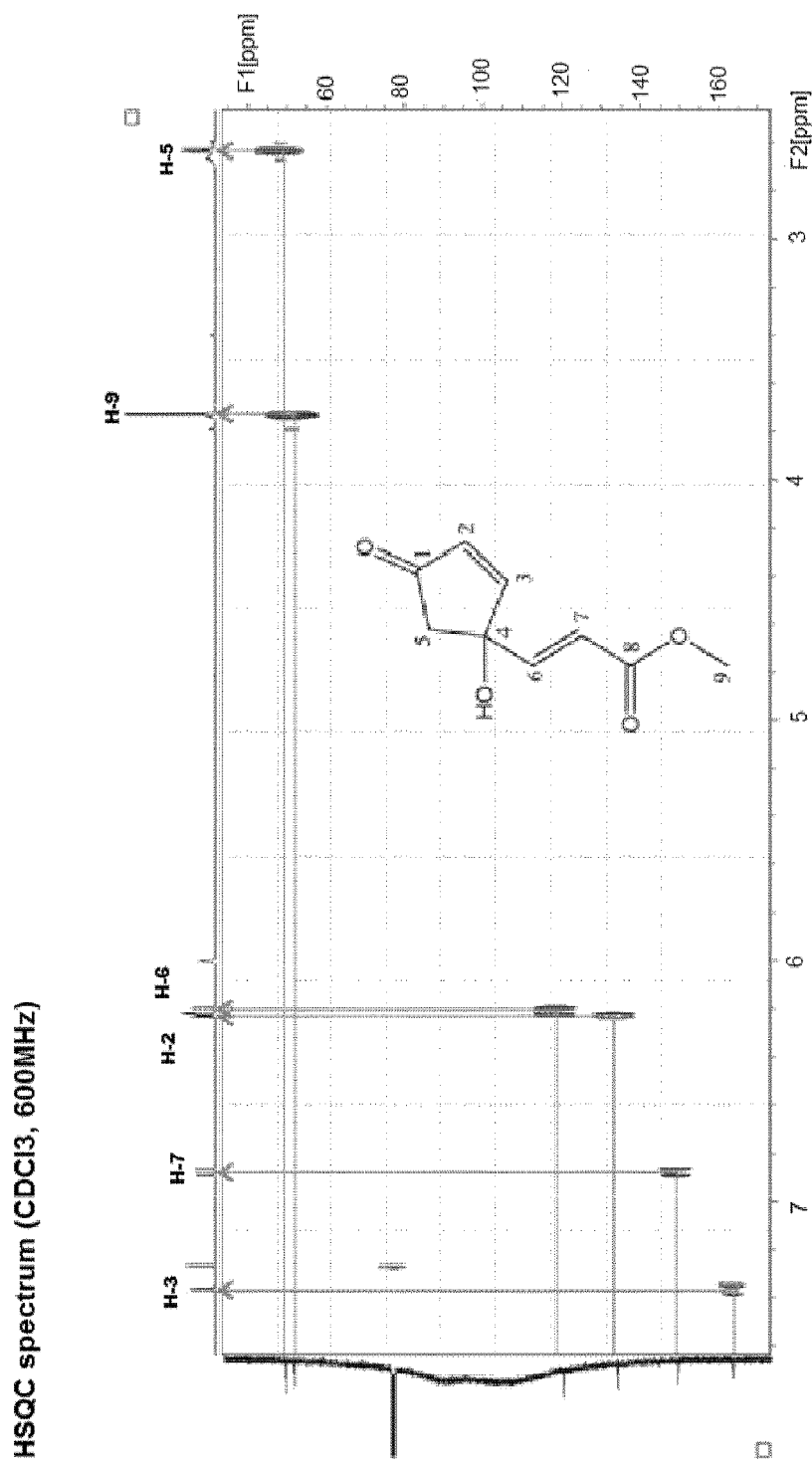
Figure 4:
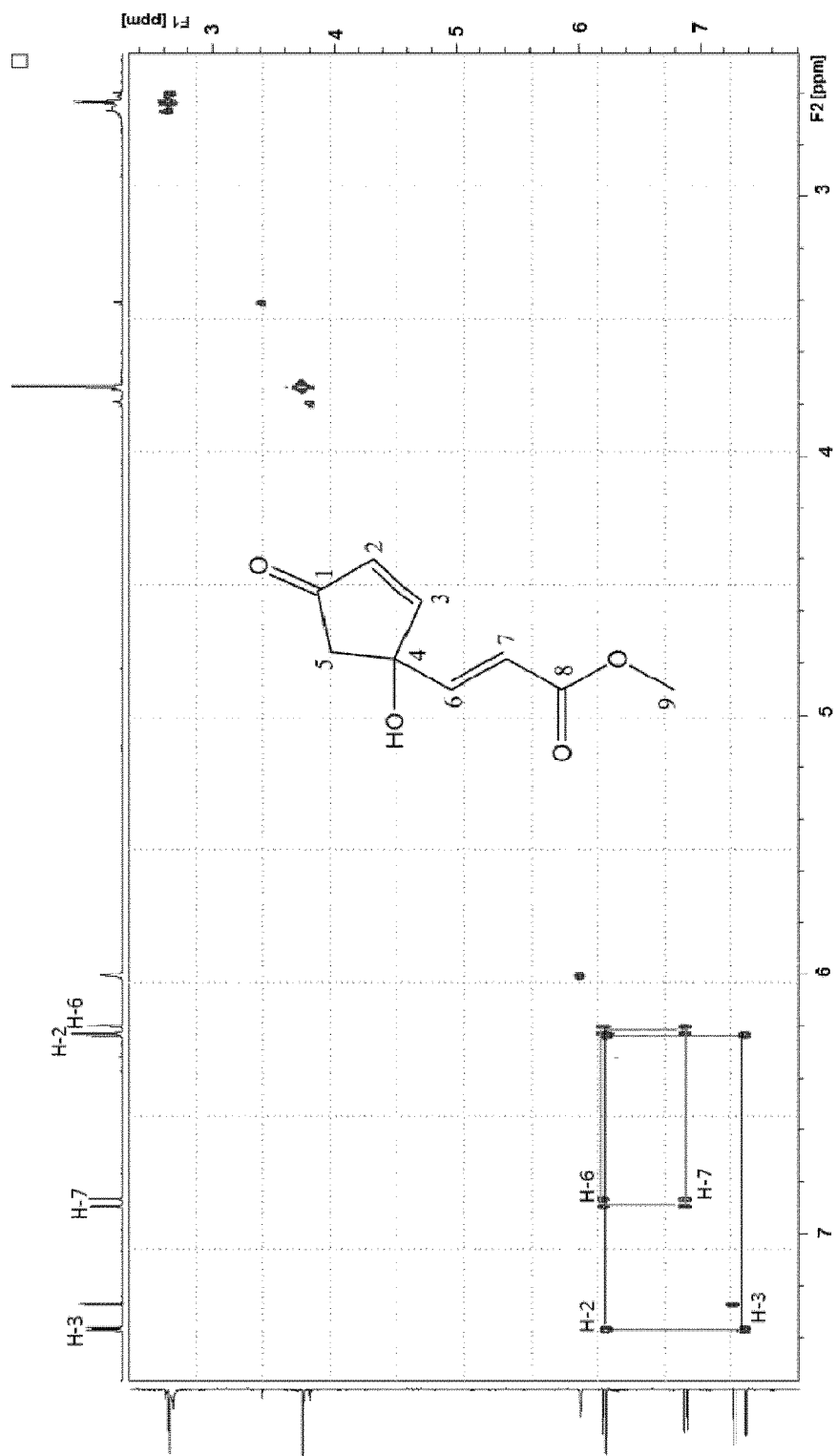
Figure 5:
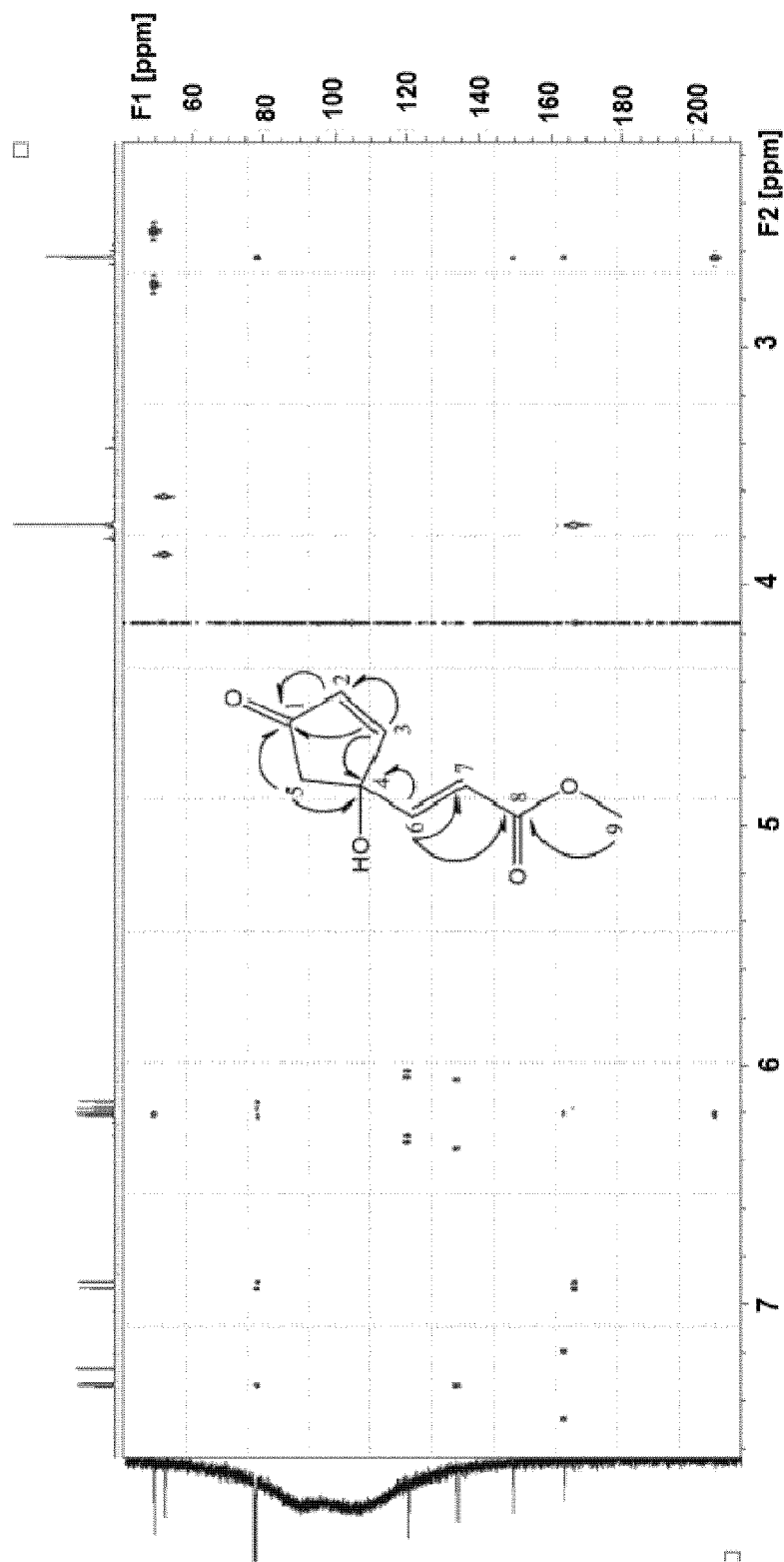

Target bacterium, *Escherichia coli* ATCC 25922
CP 30, 30 µg of chloramphenicol

Target bacterium, *Klebsiella pneumoniae* ATCC 10031
CP 30, 30 µg of chloramphenicol Target bacterium, *Enterobacter cloacae* ATCC 13047
CP 30, 30 µg of chloramphenicol Target bacterium, *Acinetobacter baumannii* ATCC 19606
CP 10, 10 µg of gentamycin Target bacterium, *Staphylococcus aureus* ATCC 25923
CP 10, 10 µg of gentamycin

4-VINYL-2-CYCLOPENTEN-1-ONE DERIVATIVES, THE PRODUCTION THEREOF, AND THE USE OF SAME AS AN ANTIBIOTIC AGENT

CROSS-REFERENCE TO RELATED APPLICATIONS

This application is a U.S. National Stage Application pursuant to 35 U.S.C. §371 of International Patent Application PCT/EP2015/059999, filed on May 6, 2015, and published as WO 2015/169876 on Nov. 12, 2015, which claims priority to French Patent Application 1454090, filed on May 6, 2014, all of which are incorporated herein by reference in their entireties for all purposes.

The present invention relates to novel 4-vinyl-2-cyclopenten-1-one derivatives, the production thereof, and the use of same as an antibiotic agent.

Infectious diseases are the leading cause of morbidity and mortality worldwide. Infections involving germs that are resistant to current treatments pose a great public health problem and generate an exorbitant increase in treatment costs estimated at 62 billion euros. In Europe, 6.2% of patients who spend more than two days in intensive care contract lung infections and 3.0% contract blood infections. Seventy percent of antibiotics approved by the United States Food and Drug Administration (FDA), and more than 80% of known antibiotics, are naturally occurring. These antibiotics have been isolated mainly from microorganisms (filamentous bacteria and fungi), an inexhaustible resource for the discovery of antibiotics, and preferentially broad-spectrum antibiotics, effective against multiple community-acquired and nosocomial infections.

The present application concerns a novel family of antibiotic molecules of general formula (I)

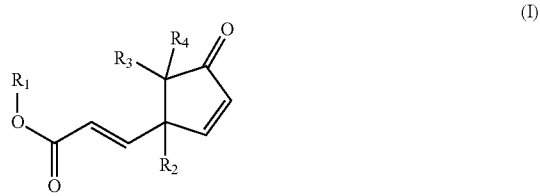

wherein:
$R_1$ is a hydrogen atom or a $C_1$ to $C_4$ alkyl radical;
$R_2$ is a $C_1$ to $C_4$ hydroxyl or alkoxyl radical, and
$R_3$ and $R_4$ are independently a hydrogen atom or a $C_1$ to $C_4$ alkyl radical; the enantiomers and mixtures of enantiomers thereof, particularly in a racemic form.

More particularly, the present application concerns a family of antibiotic molecules of general formula (Ia)

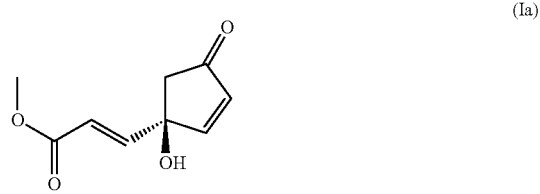

The compound of formula (Ia) was isolated from the filamentous fungus *Trichoderma*, in particular the species *atroviride*. The *Trichoderma* LMA strain used was deposited at the CNCM. This molecule was isolated and tested under specific conditions including:

1. Culturing *Trichoderma*, in particular *Trichoderma atroviride*,
2. Capture in situ, during culture, of the natural molecules produced by *Trichoderma* (natural products, secondary metabolites). This capture of molecules is carried out by means of a protocol which is known but little used in the field called "solid-phase extraction" (SPE),
3. Isolating and purifying the compound of formula (Ia) and identifying the chemical structure thereof,
4. Performing biological tests to show antibiotic activities.

Culturing *Trichoderma* begins with a Petri dish on which the microorganism grows, with the spores and mycelial fragments being collected without distinction by scraping the surface of the agar dish with a sterile liquid, preferentially liquid culture medium.

The spores and mycelium are then spread on or introduced into solid or liquid microorganism culture medium, preferentially liquid and preferentially potato dextrose broth (PDB) medium composed of potato extracts and sugar, the composition of which, for example, is as follows: 4 g/L potato starch, 20 g/L dextrose.

The fungal strain is cultured at a temperature between 0° C. and 50° C., preferentially between 20° C. and 37° C., and preferentially at 30° C. with either rotary stirring or stirring using a motor-driven turbine at between 25 and 300 revolutions per minute, preferentially at a speed of 150 revolutions per minute.

The culture is aerated continuously either by spontaneous aeration by oxygen contained in the ambient air, or by forced aeration by oxygen injection, for example that contained in compressed air. The culture thus described can be prepared in any solid or liquid microbiological culture device known to persons skilled in the art, preferentially in Erlenmeyer flasks or fermentors irrespective of their dimensions or sizes. The culture period should correspond to the maximum production of the molecule, which can vary from 1 to 15 days, preferentially from 3 to 7 days, and more preferentially is 5 days.

The in situ capture, during culture, of the natural molecules produced by *Trichoderma* is carried out by means of a protocol little used in the field called "in situ solid-phase extraction" (in situ SPE). This protocol consists in introducing an inert solid element during culture of the microorganism capable of trapping the molecules of interest released by the latter throughout the culture period. Ideally, this protocol involves resins of various types, and preferentially neutral resins such as those described in the following table, and preferentially nonpolar resins composed of polystyrene-divinylbenzene (PS-DVB) copolymers of the XAD type, and preferentially the resin XAD-16. The resin is washed with aqueous solution before use and collected by either decantation or filtration. The resin is then introduced into the culture medium in a sterile manner, either before or after sterilization thereof. Preferentially, the resin is introduced into the culture medium before sterilization then sterilized at the same time as the medium. The quantity of resin varies from 1 g/L to 100 g/L, preferentially between 10 g/L and 50 g/L, and preferentially is 30 g/L.

| Examples of resins | Matrix | Surface area (m²/g) | Particle size (mm) | Porosity (ml/ml) |
|---|---|---|---|---|
| XAD 7-HP | Acrylic ester | 450 | 0.43-0.69 | 1.4 |
| XAD 4 | Polystyrene DVB | ≥725 | 0.49-0.69 | ≥0.5 |
| Diaion HP-20 | Polystyrene DVB | 600 | >0.25 | 1.3 |
| XAD 16 | Polystyrene DVB | ≥800 | 0.56-0.71 | ≥0.55 |
| Sepabeads | Polystyrene DVB | 1000 | >0.25 | 1.2 |

With regard to isolating and purifying the compound of formula (Ia) and identifying the chemical structure thereof, the resin is collected alone or mixed with the biomass, by any technique for separating a solid matrix from a liquid container, when the *Trichoderma* culture has run for the time necessary for optimal production of the compound of formula (Ia). These methods known to persons skilled in the art include, but are not limited to, all means and techniques of filtration, centrifugation, decantation or drying. Preferentially, the resin alone or mixed with the biomass is collected by spontaneous or forced vacuum filtration, preferentially on a porous filter irrespective of its type and preferentially on an inert material.

The resin is then treated either after separation thereof from the biomass, or in mixture with the biomass. Molecules captured by the resin are collected by contacting same with a solvent irrespective of its type, preferably an organic solvent, and preferably dichloromethane or methanol, several times until the totality of the molecules of interest is collected. The solvent having dissolved the molecules of interest is then collected by filtration then evaporated by various techniques known to persons skilled in the art. The result is a residue which contains, inter alia, the molecule of interest of formula (Ia) mixed with other molecules produced by the microorganism, or initially present in the culture medium. The presence of the molecule of interest in this mixture is confirmed by chromatographic or spectrometric analyses known to persons skilled in the art, among which are the various techniques of chromatography, nuclear magnetic resonance or mass spectrometry. Preferably, the presence of the compound of formula (Ia) is detected by means of high-performance liquid chromatography (HPLC) coupled to PDA, ELS and mass spectrometry type detectors.

The target molecule of formula (Ia) is then purified from the total residue by chromatographic techniques known to persons skilled in the art including, but not limited to, chromatography on a silica column or a reverse-phase column, at atmospheric pressure or under pressure. Preferentially the molecule of the compound of formula (Ia) is pre-purified by chromatography on a normal silica column then purified by preparative HPLC under the following conditions: normal-phase chromatography on silica with a heptane/ethyl acetate (9:1) solvent mixture for 20 minutes at a flow rate of 30 mL/min, then preparative HPLC on a C18 reverse-phase column using a linear gradient of water and acetonitrile ranging from 0% to 100% acetonitrile in 10 minutes followed by a stage with 100% acetonitrile for 5 minutes at a flow rate of 4 mL/min. After lyophilization, 12 mg of the compound of formula (Ia) was obtained from 8 L of culture.

The structure of the molecule of the compound of formula (Ia) was determined by spectroscopic methods. The spectra and other analytical data are presented in the appended figures.

The NMR structural analyses (FIGS. 1 to 5) correlated with the data derived from HR-ESI-MS (high-resolution mass spectrometry) made it possible to determine the following empirical formula $C_9H_{10}O_4$ of molecular mass 182.0574.

$^{13}C$ NMR (FIG. 2) shows the presence of nine signals (49.4, 51.7, 77.7, 120.2, 133.9, 149.2, 163.4, 166.4, 205.7 ppm), the proton spectrum (FIG. 1) shows the presence of six proton groups (2.60, 3.74, 6.17, 6.20, 6.91, 7.33 ppm).

Analysis of the HSQC spectrum (FIG. 3) correlated with the 1D $^1H$ and $^{13}C$ spectrum shows the presence of a methoxy group at 51.7 ppm, a methylene group at 49.4 ppm and four alkene groups at 120.2, 133.9, 149.2 and 163.4 ppm. The absence of correlation spots for three carbons leads to the conclusion that three quaternary carbons are present: one ketone-type at 205.4 ppm, one ester- or lactone-type at 166.4 ppm and one tertiary alcohol-type at 77.7 ppm.

The COSY spectrum (FIG. 4) shows correlations between the alkene protons demonstrating the existence on the molecule of two ethylenic-type unsaturations.

The structure of the molecule of the compound of formula (Ia) is confirmed by the correlations of the HMBC spectrum (FIG. 5) and the long-range scalar interactions thereof summarized in the table below.

| Carbon number | $\delta_c$ (ppm) | HSQC | $\delta_H$ (ppm) | HMBC |
|---|---|---|---|---|
| 1 | 205.7 | C | — | H2; H3; H5 |
| 2 | 133.6 | CH | 6.20 d (5.5 Hz) | H3; H5 |
| 3 | 163.4 | CH | 7.33 d (5.5 Hz) | H2; H5 |
| 4 | 77.7 | C | — | H3; H5; H6 |
| 5 | 49.4 | CH2 | 2.63 d (5.5 Hz) | H2; H3 |
| 6 | 120.2 | CH | 6.17 d (16.0 Hz) | H3; H7 |
| 7 | 149.2 | CH | 6.91 d (16.0 Hz) | H6 |
| 8 | 166.4 | C | — | H7; H9 |
| 9 | 51.7 | CH3 | 3.74 s | |

Figure 6:
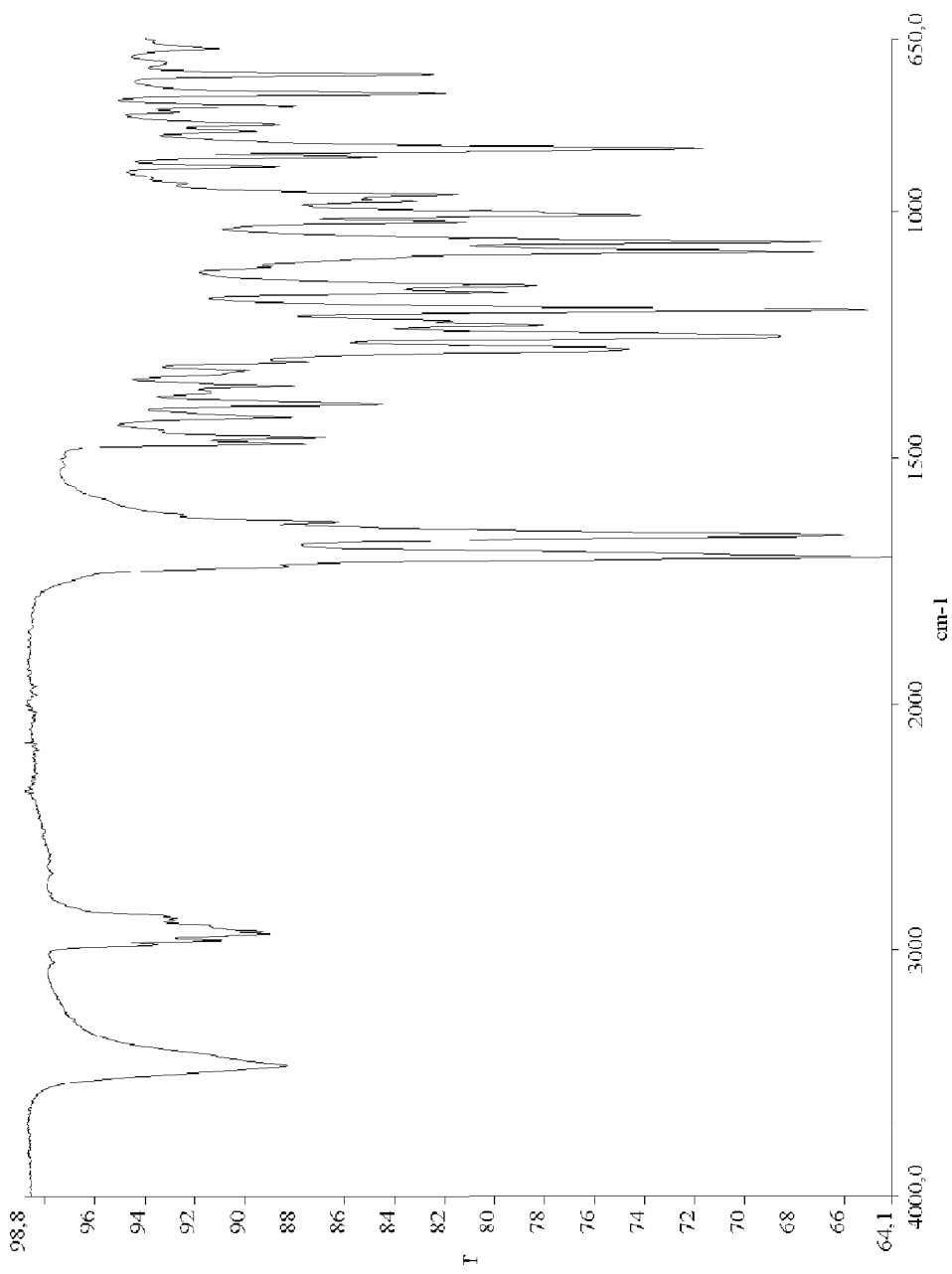

The combination of NMR data and the information obtained by mass spectrometry confirms that it is a cyclopentenone-type molecule hydroxylated at position 4 substituted with a methyl acrylate-type linear chain. The UV absorption spectrum shows a maximum at λ max=257 nm. The infrared spectrum (FIG. 6) shows absorption bands which reinforce the presence of a ketone, an alcohol and double bonds. The sign of the optical rotation measured for the molecule of the compound of formula (Ia) $[\alpha]_D^{20}$=+42.6 (20 mg/10 mL $CH_2Cl_2$) was compared with that of similar molecules such as natural trichodenone A $[\alpha]_D^{20}$=+56 which has a positive optical rotation and R stereochemistry confirmed by enantioselective total synthesis (Tetrahedron Asymmetry 2000, 11 (3711-3725).

The compounds of formulas (I) and (Ia) can also be synthesized according to the reaction scheme mentioned below.

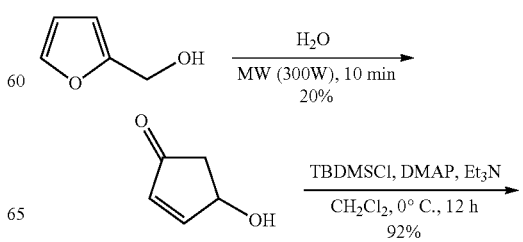

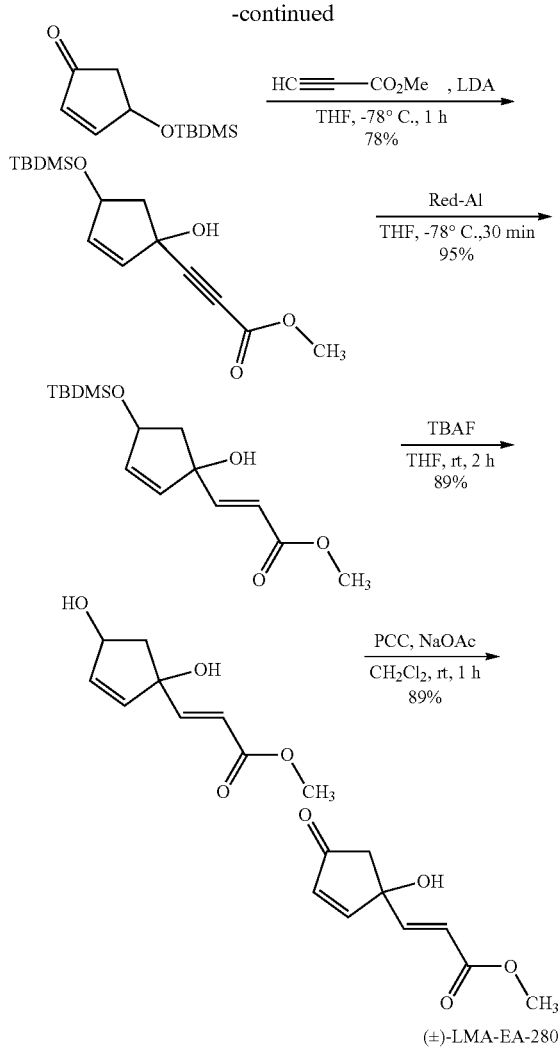

MW: MicroWave
LDA: Lithium Diisopropylamide
n-BuLi: n-ButylLithium
THF: Tetrahydrofuran
RT: Room Temperature
PCC: Pyridinium ChloroChromate
Red-Al®: sodium bis(2-methoxyethoxy)aluminumhydride Reaction Scheme for Producing the Compound of Formula (Ia)

The various compounds of formula (I) may be obtained according to the reaction scheme above by selecting the initial reaction compounds substituted in a manner corresponding to the compound of formula (I) to be produced. In particular, groups $R_3$ and $R_4$ may be introduced in the first step by selecting the appropriate substituent on the furfuryl alcohol chain (Microwave- or Microreactor-Assisted Conversion of Furfuryl Alcohols into 4-Hydroxy-2-cyclopentenones, K. Ulbrich et al., Synlett 2010, No. 13, pp. 2037-2040) or subsequently on in the synthetic sequence, in particular to transform the hydroxy radical into corresponding alkoxy $OR_2$.

Once purified, the molecule of the compound of formula (Ia) is redissolved in suitable solvents and at a suitable concentration, preferentially in dimethyl sulfoxide (DMSO) at a concentration of 10 mg/ml. This initial solution is then diluted according to the various biological tests to be performed. Two series of tests were carried out.

Tests for cytotoxicity on a KB cancer cell line (carcinoma) and an equivalent line of non-cancerous MRC5 cells. The following table presents the percentage of inhibition of growth by the molecule of the compound of formula (Ia) at concentrations of 1 and 10 micromolar. From this result, it emerges that at the concentrations used no cytotoxicity is observed against tumor cells nor against healthy cells.

|      | $10^{-5}$ M | $10^{-6}$ M |
|------|-------------|-------------|
| KB   | 0 ± 9       | 0 ± 10      |
| MRC5 | 2 ± 12      | 1 ± 3       |

The molecule of the compound of formula (Ia) was used in antibiotic tests, employing the inhibition zone technique, on various Gram-positive and Gram-negative bacteria, in the amount of 100 µg. In parallel, similar tests are carried out with control antibiotics in varying amounts depending on the antibiotic, either 10 µg or 30 µg.

| Target microorganism | Inhibition zone for 100 µg of the compound of formula (Ia) | Reference antibiotic and amount deposited | Inhibition zone by the reference antibiotics (cm) |
|---|---|---|---|
| *Escherichia coli* (ATCC 25922) | 2.7 | Chloramphenicol (30 µg) | 1.0 |
| *Klebsiella pneumoniae* (ATCC 1001) | 2.9 | Chloramphenicol (30 µg) | 2.5 |
| *Enterobacter cloacae* (ATCC 13047) | 1.2 | Chloramphenicol (30 µg) | 1.5 |
| *Micrococcus luteus* (ATCC 10240) | 3.2 | Chloramphenicol (30 µg) | 3.2 |
| *Bacillus subtilis* (ATCC 6633) | 2.7 | Gentamycin (10 µg) | 1.2 |
| *Streptococcus pneumoniae* (ATCC 49619) | 2.0 | Penicillin (30 µg) | 3.5 |
| *Acinetobacter baumannii* (ATCC 19606) | 3.2 | Gentamycin (10 µg) | 0.9 |
| *Pseudomonas aeruginosa* (ATCC 27853) | — | Gentamycin (10 µg) | 1.3 |
| *Staphylococcus aureus* (ATCC 25923) | 3.0 | Gentamycin (10 µg) | 1.2 |

Figure 7:
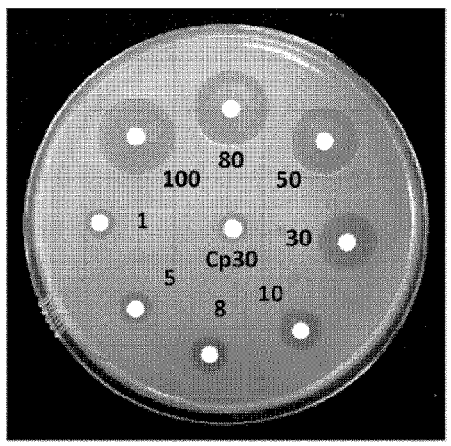
Figure 7:
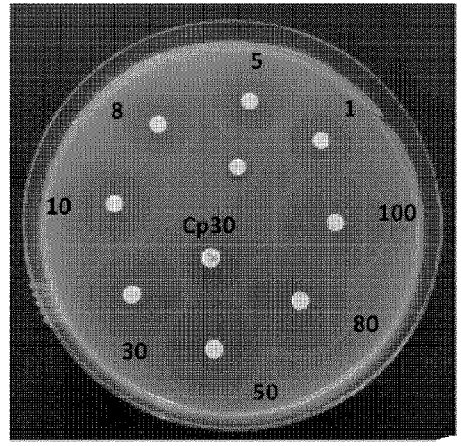
Figure 7:
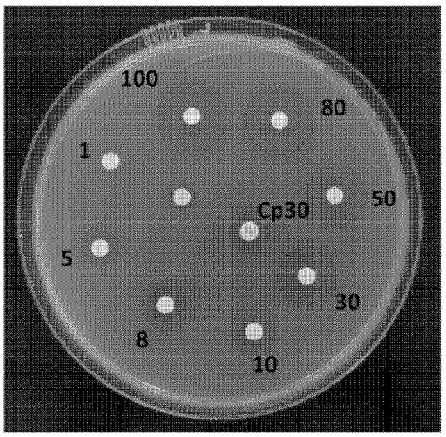
Figure 7:
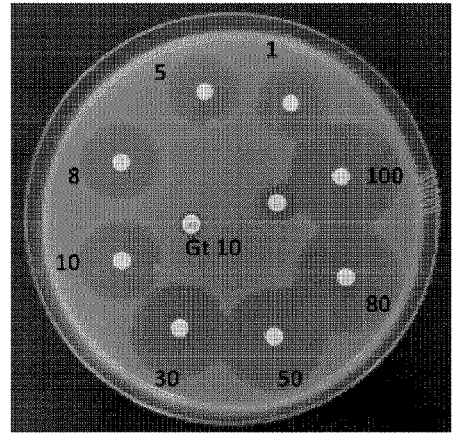
Figure 7:
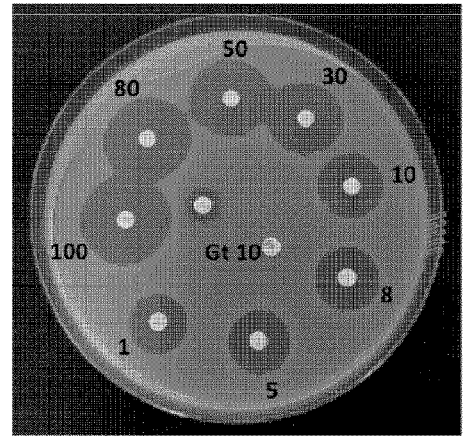

Appended FIG. 7 shows that the antibiotic activity of the compound of formula (Ia) is dose-dependent. FIG. 7 illustrates the antibiotic activity of the compound of formula (Ia) on various target pathogenic microorganisms in amounts of 1 to 100 µg in comparison with chloramphenicol and gentamycin at 30 µg and 10 µg, respectively. It shows in the case of *Escherichia coli* ATCC 25922, for example, that compound (Ia) has much higher activity than that of chloramphenicol. Indeed, inhibition by 1 µg of the compound of formula (Ia) is equivalent to that obtained with 30 µg of chloramphenicol. The same observations and conclusions can be made for all the strains that are sensitive to the compound of formula (Ia) as shown in FIG. 7. That shows that in addition to the broad spectrum of sensitive pathogenic bacteria, the molecule of the compound of formula (Ia) is effective in very small amounts.

An example of the production of the compound of formula Ia is provided below for purposes of illustration.

EXAMPLE 1

1.1. General Procedure

Unless otherwise specified, all the reactions were carried out under an inert atmosphere of argon, in glassware first dried in a 120° C. oven.

1.1.1. Solvents

Tetrahydrofuran (THF) was distilled under argon over sodium/benzophenone. Dichloromethane ($CH_2Cl_2$) was distilled under argon over calcium hydride ($CaH_2$). Unless otherwise specified, all the reagents employed are commercial reagents of reagent-grade quality.

1.1.2. TLC Analysis

The crude reaction mixtures obtained, the fractions and the purified products were analyzed by thing layer chromatography (TLC) on silica gel plates (Merck 60 $F_{254}$ 0.2-mm thickness on aluminum sheets). The plates are observed under a UV lamp (at 254 and 312 nm) before being developed by spraying with ammonium molybdate solution $(NH_4)_2Mo_2O_7$ (100 g/L in 10% sulfuric acid) and heating.

Retention factor is defined as the ratio between the distance covered by the compound on the plate and the solvent front.

1.1.3. Purification

Purification of the reaction mixtures was carried out by flash chromatography on silica gel (Merck 60 (35-70 μm)).

1.1.4. Spectroscopic Analyses

1.1.4.1 High-Resolution Mass Spectrometry

High-resolution mass spectra were obtained on a mass spectrometer equipped with an atmospheric pressure ionization source (ESI) and with a time of flight (TOF)-type mass analyzer (LCT®, Waters).

1.1.4.2 Nuclear Magnetic Resonance (NMR)

Nuclear magnetic resonance experiments were carried out on Bruker Avance 300 and 500 devices using deuterated chloroform ($CDCl_3$). Chemical shifts are expressed in parts per million (ppm) and calibrated relative to the reference solvent. Coupling constants are expressed in hertz (Hz). Signal multiplicity is expressed by the following abbreviations: s (singlet), bs (broad singlet), d (doublet), dd (doublet of doublets), t (triplet), m (multiplet), q (quadruplet). Attribution of the proton and carbon signals was carried out from one-dimensional (1D) $^1H$ and $^{13}C$, and two-dimensional (2D) $^1H$-$^1H$ COSY, $^1H$-$^{13}C$ HSQC or HMQC, $^1H$-$^{13}C$ HMBC, $^1H$-$^1H$ NOESY experiments. NMR spectra are processed using the dedicated TopSpin software (Brucker).

1.1.4.3 Optical Rotation

The optical rotations of the compounds were measured using a Jasco™ P1010 polarimeter equipped with the Spectro Manager software. The monochromatic light source is the sodium D-line. The experiments were conducted with a 100 mm, 350 μL quartz cuvette and the products were dissolved in methanol.

1.1.4.4 Infrared Spectroscopy

Infrared (IR) absorption spectra of the described compounds were measured on the Perkin-Elmer Spectrum 100 FT-IR spectrometer. The device is equipped with the Spectrum software (version 6.3.5) from Perkin-Elmer. The compounds were produced in solution in methanol then dried with compressed air. Absorption bands are given in $cm^{-1}$.

1.2. Synthesis of Compounds 2 to 7

Compound 2: 4-hydroxycyclopent-2-enone

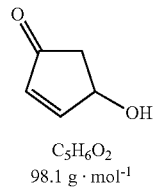

$C_5H_6O_2$
98.1 g·mol$^{-1}$

A solution of furfuryl alcohol (1) (3.0 ml, 34.7 mmol) in distilled water (5 ml) is placed in a microwave tube (CEM Discover) and heated in a closed vessel at 300 W for 10 minutes. After cooling and decanting, the aqueous phase is collected and the residue washed with 2×5 ml of distilled water. The aqueous phases are combined and washed by liquid-liquid extraction with ethyl acetate (2×50 ml). The aqueous phase is then concentrated to give 668 mg (20%) of compound 2 in the form of an orange-red oil. The product obtained does not require purification before being employed in the following reaction (K. Ulbrich, P. Kreitmeier, O. Reiser, Synlett. 2010, 13, 2037-2040)

Rf=0.32 (Heptane/AcOEt, 2:8)

$^1H$ NMR (300 MHz, $CDCl_3$): $\delta_H$ (ppm) 7.57 (dd, 1H, J=2.3 Hz, J=5.7 Hz), 6.22 (dd, 1H, J=1.1 Hz, J=5.7 Hz), 5.06-5.02 (m, 1H), 2.77 (dd, 1H, J=6.1 Hz, J=18.5 Hz), 2.27 (dd, 1H, J=2.1 Hz, J=18.5 Hz).

$^{13}C$ NMR (75 MHz, $CDCl_3$): $\delta_C$ (ppm) 207.1, 163.7, 135.0, 70.3, 44.2.

HRMS (ESI): m/z calculated for $C_5H_7O_2$ [M+H]$^+$ 99.0446 experimental value 99.0449

Compound 3: 4-((tert-butyldimethylsilyl)oxy)cyclopent-2-enone

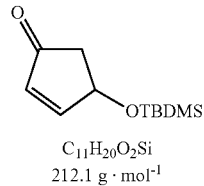 [SMILES: CC(C)(C)[Si](C)(C)OC1C=CC(=O)C1]

$C_{11}H_{20}O_2Si$
212.1 g·mol$^{-1}$

Compound 2 (334 mg, 3.41 mmol) is dissolved in dichloromethane (6 ml). The reaction mixture is then held at 0° C. Triethylamine (700 μl, 4.78 mmol), DMAP (33 mg, 0.27 mmol) and tert-butyldimethylsilyl chloride (1.0 M in THF, 3.75 ml) are then added. The reaction is held at 0° C. with stirring for 12 hours. After adding distilled water (10 ml), the medium is extracted with dichloromethane (3×20 ml). The organic phase is dried over anhydrous sodium sulfate, then evaporated to dryness. The crude reaction mixture obtained is purified by flash chromatography on silica gel (eluent: heptane/AcOEt, 80:20) to give 664 mg (92%) of compound 3 in the form of a transparent oil (white crystals at 4° C.) (K. Ulbrich, P. Kreitmeier, O. Reiser, Synlett. 2010, 13, 2037-2040).

Rf=0.53 (Heptane/AcOEt, 3:7)

$^1H$ NMR (300 MHz, $CDCl_3$): $\delta_H$ (ppm) 7.46 (dd, 1H, J=2.3 Hz, J=5.7 Hz), 6.19 (dd, 1H, J=1.1 Hz, J=5.7 Hz), 5.01-4.98 (m, 1H), 2.71 (dd, 1H, J=6.1 Hz, J=18.5 Hz), 2.25 (dd, 1H, J=2.2 Hz, J=18.5 Hz), 0.91 (s, 9H), 0.14 (s, 3H), 0.13 (s, 3H).

$^{13}$C NMR (75 MHz, CDCl$_3$): $\delta_C$ (ppm) 206.5, 163.8, 134.4, 70.9, 45.0, 25.7, 18.1, −4.8

HRMS (ESI): m/z calculated for C$_{22}$H$_{41}$O$_4$Si$_2$ [2M+H]$^+$ 425.2583 experimental value 425.2601

Compound 4: methyl 3-(4-((tert-butyldimethylsilyl)oxy)-1-hydroxycyclopent-2-en-1-yl)propiolate

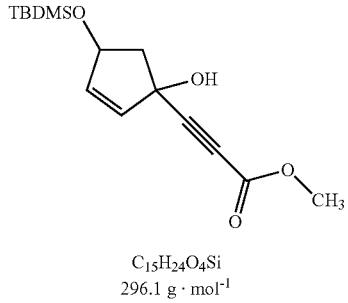 [SMILES: COC(=O)C#CC1(O)C=CC(O[Si](C)(C)C(C)(C)C)C1]

C$_{15}$H$_{24}$O$_4$Si
296.1 g·mol$^{-1}$ n-Butyl lithium (1.6 M in hexane, 2.14 ml, 1.1 eq) is added to a solution of diisopropylamine (529 μl, 1.2 eq) in 10 ml of THF and held at −78° C. At the end of 30 minutes, methyl propiolate (277 μl, 1.0 eq) is added to the LDA solution obtained beforehand. The reaction is held at −78° C. with stirring for 1 hour. Compound 3 (660 mg, 3.11 mmol) is dissolved in 5 ml of THF at −78° C. then the solution is slowly added to the lithium acetylide solution generated beforehand. The reaction is held at −78° C. with stirring for 1 hour. After adding 20 ml of saturated NH$_4$Cl solution, the mixture is extracted with 3×50 ml of ethyl acetate. The organic phase is dried over anhydrous sodium sulfate, then evaporated to dryness. The crude reaction mixture obtained is purified by flash chromatography on silica gel (eluent: heptane/AcOEt, 80:20) to give 718 mg (78%) of compound 4 in the form of a yellow translucent oil.

Rf=0.44 (Heptane/AcOEt, 6:4)

$^1$H NMR (300 MHz, CDCl$_3$): $\delta_H$ (ppm) 5.99 (dd, 1H, J=1.7 Hz, J=5.4 Hz), 5.92 (d, 1H, J=5.5 Hz), 4.83 (t, 1H, J=5.4 Hz), 3.78 (s, 3H), 2.87 (dd, 1H, J=6.7 Hz, J=13.6 Hz), 2.02 (dd, 1H, J=4.3 Hz, J=13.7 Hz), 0.90 (s, 9H), 0.10 (s, 6H).

$^{13}$C NMR (75 MHz, CDCl$_3$): $\delta_C$ (ppm) 153.8, 138.5, 134.7, 88.2, 75.6, 74.9, 52.8, 51.0, 25.8, 18.0, −4.7.

HRMS (ESI): m/z calculated for C$_{15}$H$_{23}$O$_3$Si [M−H$_2$O+H]$^+$ 279.1416 experimental value 279.1414

Compound 5: (E)-methyl 3-(4-((tert-butyldimethylsilyl)oxy)-1-hydroxycyclopent-2-en-1-yl)acrylate

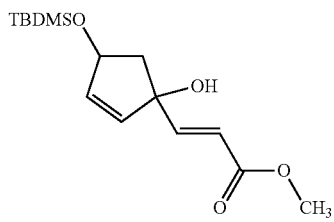

C$_{15}$H$_{26}$O$_4$Si
298.2 g·mol$^{-1}$

Compound 4 (700 mg, 2.36 mmol) is dissolved in 20 ml of distilled THF and the solution is cooled to −78° C. Commercial Red-Al solution (3.21 M in toluene, 1.54 ml, 2.0 eq) is added dropwise and the reaction is held at −78° C. with stirring for 30 minutes. After adding 20 ml of distilled water, the crude reaction mixture is extracted with 3×100 ml of ethyl acetate. The organic phase is washed with 10 ml of saturated NaHCO$_3$ solution, then dried over anhydrous sodium sulfate before being filtered and evaporated to dryness. The residue obtained is purified by flash chromatography on silica gel (eluent: heptane/AcOEt, 80:20) to give 668 mg (95%) of compound 5 in the form of a light yellow translucent oil.

Rf=0.63 (Heptane/AcOEt, 6:4)

$^1$H NMR (300 MHz, CDCl$_3$): $\delta_H$ (ppm) 6.84 (d, 1H, J=15.4 Hz), 6.09 (d, 1H, J=15.6 Hz), 5.97 (dd, 1H, J=2.0 Hz, J=5.4 Hz), 5.77 (d, 1H, J=5.5 Hz), 4.80-4.77 (m, 1H), 3.75 (s, 3H), 2.52 (dd, 1H, J=6.5 Hz, J=13.8 Hz), 1.87 (dd, 1H, J=3.9 Hz, J=13.8 Hz), 0.90 (s, 9H), 0.10 (s, 6H).

$^{13}$C NMR (75 MHz, CDCl$_3$): $\delta_C$ (ppm) 167.4, 150.5, 137.4, 136.7, 118.5, 82.9, 75.3, 51.6, 49.8, 25.8, 18.1, −4.7.

HRMS (ESI): m/z calculated for C$_{15}$H$_{25}$O$_3$Si [M−H$_2$O+H$^+$] 281.1573 experimental value 281.1562

Compound 6: (E)-methyl 3-(1,4-dihydroxycyclopent-2-en-1-yl)acrylate

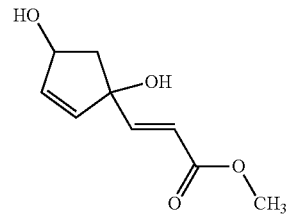

C$_9$H$_{12}$O$_4$
184.2 g·mol$^{-1}$

Compound 5 (650 mg, 2.18 mmol) is dissolved in 20 ml of distilled THF at room temperature. Commercial TBAF solution (1 M in THF, 4.37 ml, 2.0 eq) is added dropwise and the reaction is held at room temperature with stirring for 2 hours. After adding 10 ml of saturated NaCl solution, the reaction mixture is extracted with 3×100 ml of ethyl acetate. The combined organic phases are dried over anhydrous sodium sulfate before being filtered and evaporated to dryness. The residue obtained is purified by flash chromatography on silica gel (eluent: heptane/AcOEt, 80:20) to give 357 mg (89%) of compound 6 in the form of a translucent oil.

Rf=0.41 (Heptane/AcOEt, 3:7)

$^1$H NMR (300 MHz, CDCl$_3$): $\delta_H$ (ppm) 6.87 (d, 1H, J=15.7 Hz), 6.09 (d, 1H, J=15.6 Hz), 6.09 (dd, 1H, J=2.0 Hz, J=5.4 Hz), 5.84 (d, 1H, J=5.5 Hz), 4.85-4.81 (m, 1H), 3.76 (s, 3H), 2.60 (dd, 1H, J=6.7 Hz, J=14.3 Hz), 1.91 (dd, 1H, J=3.5 Hz, J=14.3 Hz).

$^{13}$C NMR (75 MHz, CDCl$_3$): $\delta_C$ (ppm) 167.1, 150.8, 137.7, 136.9, 118.6, 83.0, 75.2, 51.7, 48.9.

HRMS (ESI): m/z calculated for C$_9$H$_{11}$O$_3$ [M−H$_2$O+H$^+$] 167.0708 experimental value 167.0700

Compound 7: (E)-methyl 3-(1-hydroxy-4-oxocyclo-pent-2-en-1-yl)acrylate (±)-LMA-EA-2801

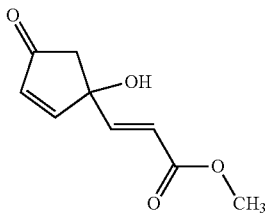

$C_9H_{10}O_4$
182.2 g · mol$^{-1}$

The compound (350 mg, 1.92 mmol) is dissolved in 15 ml of distilled $CH_2Cl_2$ at room temperature, before adding thereto sodium acetate (313 mg, 1.2 eq) and pyridinium chlorochromate (PCC, 497 mg, 1.2 eq). The reaction is held at room temperature with stirring for 1 hour. The reaction mixture is filtered on a Celite cartridge and the filtrate obtained is evaporated to dryness. The residue is then purified by flash chromatography on silica gel (eluent: heptane/AcOEt, 60:40) to give 296 mg (84%) of compound 7 in the form of a translucent oil.

Rf=0.38 (Heptane/AcOEt, 3:7)

$^1$H NMR (300 MHz, CDCl$_3$): $\delta_H$ (ppm) 7.35 (d, 1H, J=5.3 Hz), 6.94 (d, 1H, J=15.8 Hz), 6.27 (d, 1H, J=5.4 Hz), 6.18 (d, 1H, J=15.8 Hz), 3.77 (s, 3H), 2.67 (d, 1H, J=12.0 Hz).

$^{13}$C NMR (75 MHz, CDCl$_3$): $\delta_C$ (ppm) 205.0, 166.4, 162.6, 148.5, 134.6, 120.5, 78.3, 51.9, 49.3.

HRMS (ESI): m/z calculated for $C_9H_9O_3$ [M−H$_2$O+H$^+$] 165.0552 experimental value 165.0550

Separation of Enantiomers (+)-LMA-EA-2801 and (−)-LMA-EA-2801

Compound 7 was analyzed by chiral HPLC equipped with a UV detector in order to detect the two enantiomers and to be able to separate same. (Waters Alliance 2695 HPLC system coupled to a Waters 996 PDA detector; Daicel Chiral Technologies IC chiral column (4.6×250 mm, 5 µm); eluent: n-heptane/isopropanol, 80:20).

Based on the analytical data, the separation of the enantiomers was then carried out by preparative SFC.

(Waters Chain Investigator II equipped with a 2420 ELS detector and a 2996 PDA detector; Daicel Chiral Technologies IC chiral column (4.6×250 mm, 5 µm); eluent: supercritical $CO_2$/isopropanol/methanol, 80:10:10).

The optical rotations of the two enantiomers were measured and compare with that obtained for the naturally-occurring optically-pure compound $[\alpha]^{20}_D$ (−)-LMA-EA-2801: −45.7

$[\alpha]^{20}_D$ (+)-LMA-EA-2801: +40.9 (value consistent with that obtained for the naturally-occurring optically-pure compound of formula Ia)

The present invention relates to compounds of formula (I) or (Ia) for use as an antibiotic agent, particularly as a broad-spectrum antibiotic agent, and notably against multiresistant Gram-positive and Gram-negative pathogenic bacteria.

The present invention relates to a pharmaceutical composition containing as active ingredient at least a compound of formula (I) or (Ia) associated with a pharmaceutically acceptable excipient, which may be easily determined based on the general knowledge of persons skilled in the art according to the route of administration selected.

The invention claimed is:

1. A method of treating a bacterial infection in a subject comprising administering to a subject in need thereof, an effective amount of a compound of the following general formula (I):

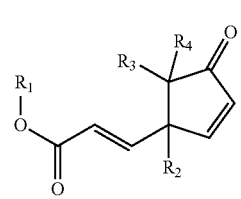

(I)

wherein:
$R_1$ is a hydrogen atom or a $C_1$ to $C_4$ alkyl radical;
$R_2$ is a $C_1$ to $C_4$ hydroxyl or alkoxyl radical, and
$R_3$ and $R_4$ are independently a hydrogen atom or a $C_1$ to $C_4$ alkyl radical;
the enantiomers and mixtures of enantiomers thereof;
and wherein the infection is a bacterial infection selected from among the group consisting of an *Escherichia, Klebsiella, Enterobacter, Micrococcus, Bacillus, Streptococcus, Acinetobacter*, and *Stapylococcus* infection.

2. The method according to claim 1, wherein the compound is a compound of the following formula (Ia):

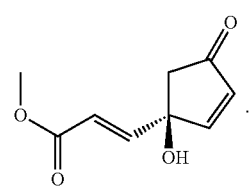

(Ia)

3. The method according to claim 1 or claim 2, wherein the compound is an antibiotic agent.

4. The method according to claim 3, wherein the compound is a broad-spectrum antibiotic agent.

5. The method according to claim 3, wherein the compound is an antibiotic agent against multiresistant Gram-positive and Gram-negative pathogenic bacteria.

6. The method of claim 1 or claim 2, wherein the compound is comprised in a pharmaceutical composition characterized in that it contains as an active ingredient at least a compound of formula (I) or (Ia) associated with a pharmaceutically acceptable excipient.

7. The method of claim 1 or claim 2, wherein the compound is administered as a racemic form.

* * * * *